(12) United States Patent
Buchman et al.

(10) Patent No.: US 12,329,827 B2
(45) Date of Patent: *Jun. 17, 2025

(54) DEVICES, COMPOSITIONS AND RELATED METHODS FOR ACCELERATING AND ENHANCING BONE REPAIR

(71) Applicants: THE REGENTS OF THE UNIVERSITY OF MICHIGAN, Ann Arbor, MI (US); THE UNIVERSITY OF KANSAS, Lawrence, KS (US)

(72) Inventors: Steven R. Buchman, Ann Arbor, MI (US); Mark Cohen, Ann Arbor, MI (US); Alexis Donneys, Ann Arbor, MI (US); Noah Nelson, Ann Arbor, MI (US); Laird Forrest, Lawrence, KS (US); Ti Zhang, Lawrence, KS (US); Qiuhong Yang, Lawrence, KS (US)

(73) Assignees: THE REGENTS OF THE UNIVERSITY OF MICHIGAN, Ann Arbor, MI (US); THE UNIVERSITY OF KANSAS, Lawrence, KS (US)

(*) Notice: Subject to any disclaimer, the term of this patent is extended or adjusted under 35 U.S.C. 154(b) by 176 days.

This patent is subject to a terminal disclaimer.

(21) Appl. No.: 17/354,514

(22) Filed: Jun. 22, 2021

(65) Prior Publication Data
US 2021/0322569 A1    Oct. 21, 2021

Related U.S. Application Data

(63) Continuation of application No. 16/063,061, filed as application No. PCT/US2016/067320 on Dec. 16, 2016, now Pat. No. 11,045,556.
(Continued)

(51) Int. Cl.
*A61K 47/69*    (2017.01)
*A61K 9/51*    (2006.01)
(Continued)

(52) U.S. Cl.
CPC ........ *A61K 47/6939* (2017.08); *A61K 9/5169* (2013.01); *A61K 31/16* (2013.01);
(Continued)

(58) Field of Classification Search
None
See application file for complete search history.

(56) References Cited

U.S. PATENT DOCUMENTS 5,217,998 A * 6/1993 Hedlund ................ A61K 31/16
514/777
6,013,679 A * 1/2000 Kuo ........................ A61L 27/20
514/777

(Continued)

FOREIGN PATENT DOCUMENTS

WO    WO 2012/140650    10/2012
WO    WO 2014/036414    3/2014
WO    WO-2014036414 A2 *    3/2014    ........... A61K 31/164

OTHER PUBLICATIONS

Stahl.com. "Crosslinkers with top-class performance and a lower environmental impact." https://www.stahl.com/polymers-brands/crosslinkers accessed Jun. 22, 2023, pp. 1-7. (Year: 2023).*

(Continued)

*Primary Examiner* — Isaac Shomer
(74) *Attorney, Agent, or Firm* — Casimir Jones, S.C.; Robert A. Goetz

(57) ABSTRACT

The present invention relates to novel therapeutic nanoparticles. In particular, the present invention is directed to nanoparticles associated (e.g., complexed, conjugated, encapsulated, absorbed, adsorbed, admixed) with angiogenesis-activating-agents, methods of synthesizing the same, devices or compositions comprising such nanoparticles, as well as systems and methods utilizing the nanoparticles (Continued)

(e.g., in therapeutic settings for enhancing and/or activating angiogenesis at targeted tissue region).

11 Claims, 10 Drawing Sheets

Related U.S. Application Data

(60) Provisional application No. 62/268,926, filed on Dec. 17, 2015.

(51) Int. Cl.

| | |
|---|---|
| A61K 31/16 | (2006.01) |
| A61K 47/61 | (2017.01) |
| A61L 27/20 | (2006.01) |
| A61L 27/50 | (2006.01) |
| A61L 27/54 | (2006.01) |
| A61L 27/58 | (2006.01) |
| A61P 19/00 | (2006.01) |
| A61P 19/08 | (2006.01) |

(52) U.S. Cl.
CPC .............. *A61K 47/61* (2017.08); *A61L 27/20* (2013.01); *A61L 27/50* (2013.01); *A61L 27/54* (2013.01); *A61L 27/58* (2013.01); *A61P 19/00* (2018.01); *A61P 19/08* (2018.01); *A61L 2300/412* (2013.01); *A61L 2300/624* (2013.01); *A61L 2300/626* (2013.01); *A61L 2400/12* (2013.01); *A61L 2430/02* (2013.01)

(56) References Cited

U.S. PATENT DOCUMENTS

| 11,045,556 B2* | 6/2021 | Buchman ............... A61K 31/16 |
| 2009/0074828 A1 | 3/2009 | Alexis et al. |
| 2011/0052715 A1 | 3/2011 | Davis et al. |
| 2017/0231910 A1* | 8/2017 | Hayes .................... A61K 9/127 206/568 |

OTHER PUBLICATIONS

Jaya Maitra and Vivek Kumar Shukla. "Cross-linking in Hydrogels—A Review." American Journal of Polymer Science, vol. 4(2), 2014, pp. 25-31. (Year: 2014).*
Koenraad de Boulle et al. "A Review of the Metabolism of 1,4-Butanediol Diglycidyl Ether-Crosslinked Hyaluronic Acid Dermal Fillers." Dermatological Surgery, vol. 39, 2013, pp. 1758-1766. (Year: 2013).*
Peter L. Gehlbach, Richard L. Purple, Philip E. Hallaway, and Bo E. Hedlund. "Polymer Conjugation Reduces Deferoxamine Induced Retinopathy in an Albino Rat Model." Investigative Ophthalmology & Visual Science, vol. 34, No. 10, Sep. 1993, pp. 102871-2877. (Year: 1993).*
Jason A. Burdick and Glenn D. Prestwich. "Hyaluronic Acid Hydrogels for Biomedical Applications." Advanced Healthcare Materials, vol. 23, 2011, pp. H41-H56. (Year: 2011).*
National Cancer Institute. "molecular weight." https://www.cancer.gov/publications/dictionaries/cancer-terms/def/molecular-weight accessed Nov. 18, 2024 (Year: 2024).*
Tao Zhou, Gunther Winkelmann, Zhi-Yuan Dai and Robert C. Hider. "Design of clinically useful macromolecular iron chelators." Journal of Pharmacy and Pharmacology, vol. 63, 2011, pp. 893-903. (Year: 2011).*
Tao Zhou, Xiao Le Kong, Zu Dong Liu, Ding Yong Liu, and Robert C. Hider. "Synthesis and Iron(III)-Chelating Properties of Novel 3-Hydroxypyridin-4-one Hexadentate Ligand-Containing Copolymers." Biomacromolecules, vol. 9, 2008, pp. 1372-1380. (Year: 2008).*

Aronson, J. Temporal and spatial increases in blood flow during distraction osteogenesis. Clinical orthopaedics and related research 301 (1994): 124-131.
Baldini, A., et al., Bone-defects healing by high-molecular hyaluronic acid: preliminary results. Ann Stomatol (Roma). Jan.-Mar. 2010; 1(1): 2-7.
Beamer, B, et al., Vascular Endothelial Growth Factor: An Essential Component of Angiogenesis and Fracture Healing. HSS journal 6.1 (2010): 85-94.
Brighton, CT, et al., Early histological and ultrastructural changes in medullary fracture callus. J BoneJointSurg73A:832-847, 1991.
Cavadias, AX, et al., An Experimental Study of the Vascular Contribution to the Callus of Fracture. Surg Gynecol Obstet 120:731-747, 1965.
Donneys, A., et al. Deferoxamine restores callus size, mineralization, and mechanical strength in fracture healing after radiotherapy. Plast Reconstr Surg. May 2013; 131(5):711e-9e.
Donneys, A., et al. Localized deferoxamine injection augments vascularity and improves bony union in pathologic fracture healing after radiotherapy. Bone 52.1 (2013):318-325.
Donneys, A., et al., Deferoxamine expedites consolidation during mandibular distraction osteogenesis. Bone 55.2 (2013): 384-390.
Donneys, A., et al., Targeting angiogenesis as a therapeutic means to reinforce osteocyte survival and prevent nonunions in the aftermath of radiotherapy. Head & neck, 2015; 37(9): 1261-1267.
Farberg, A. S., et al., Deferoxamine reverses radiation induced hypovascularity during bone regeneration and repair in the murine mandible. Bone 50.5 (2012): 1184-1187.
Farberg, A.S., et al., Deferoxamine enhances bone regeneration in mandibular distraction osteogenesis. Plastic and reconstructive surgery 133.3 (2014): 666-671.
Felice, P.A., et al., Deferoxamine administration delivers translational optimization of distraction osteogenesis in the irradiated mandible. Plastic and reconstructive surgery 132.4 (2013): 542e.
Glowacki, J., Angiogenesis in fracture repair. Clinical orthopaedics and related research 355 (1998) S82-S89.
Harten, et al., Prolyl hydroxylase domain inhibitors: a route to HIF activation and neuroprotection. Antioxidants & redox signaling 12.4 (2010): 459-480.
Huang, L., et al., Regulation of hypoxia-inducible factor 1α is mediated by an O2-dependent degradation domain via the ubiquitin-proteasome pathway. Proceedings of the National Academy of Sciences 95.14 (1998): 7987-7992.
Hunter, J. Treatise on the Blood, Inflammation, and Gunshot Wounds. Philadelphia, Thomas Bradford 1794. Table of Contents Only.
International Search Report & Written Opinion, International Patent Application No. PCT/US2016/067320, mailed Mar. 27, 2017, 14 pages.
Jiang, et al. Promotion of airway anastomotic microvascular regeneration and alleviation of airway ischemia by deferoxamine nanoparticles. Biomaterials, Oct. 2013, vol. 35, pp. 803-813.
Kelly, PJ, et al., Reaction of the Circulatory System to Injury and Regeneration. Clin Orthop 254275-288, 1990.
Kuchler, U, et al., Dimethyloxalylglycine lyophilized onto bone substitutes increase vessel area in rat calvarial defects. Clinical oral implants research 26.5 (2015): 485-491.
Laurnen, EL, et al. Blood flow, oxygen consumption, carbon-dioxide production, and blood-calcium and pH changes in tibial fractures in dogs. J Bone Joint Surg 51A:298-308, 1969.
Li et al. The effect of deferoxamine on anglogenesis and bone repair in steroid-induced osteonecrosis of rabbit femoral heads. Experimetnal Biology and Medicine, Oct. 2014, vol. 240, p. 273-280.
Liu, X., et al., Prolyl hydroxylase inhibitors protect from the bone loss in ovariectomy rats by increasing bone vascularity. Cell biochemistry and biophysics 69.1 (2014): 141-149.
Nishida, N. et al. Angiogenesis in cancer. Vascular Health and Risk Management, Sep. 2006, pp. 213-219.
Parajo, Y. et al. Hyaluronic acid/Chitosan nanoparticles as delivery vehicles for VEGF and PDGF-BB, Drug Delivery, Oct. 2010, vol. 17, pp. 596-604.
Rhinelander, FW, Tibial Blood Supply in Relation to Fracture Healing. Clin Orthop 105:34-49, 1974.

(56) References Cited

OTHER PUBLICATIONS

Rhinelander, FW, The Normal Microcirculation of Diaphyseal Cortex and Its Response to Fracture. J Bone Joint Surg 50A:784-800, 1968.
Segar, C.E., et al., Regulation of Angiogenesis and Bone Regeneration with Natural and Synthetic Small Molecules. Current pharmaceutical design 19.19 (2013): 3403-3419.
Shen et al. Prolyl hydroxylase inhibitors increase neoangiogenesis and callus formation following femur fracture in mice. Journal Orthopaedic Research, Mar. 2009, vol. 27, pp. 1298-1305.
Street, J., et al., Vascular endothelial growth factor stimulates bone repair by promoting angiogenesis and bone turnover. Proceedings of the National Academy of Sciences 99.15 (2002): 9656-9661.
Towler, D.A., The osteogenic-angiogenic interface: Novel insights into the biology of bone formation and fracture repair. Current osteoporosis reports 6.2 (2008): 67-71.
Trueta J,. the Role of the Vessels in Osteogenesis. J Bone Joint Surg 45B:402-418, 1963.
Wan, C., et al., Activation of the hypoxia-inducible factor-1α pathway accelerates bone regeneration. Proceedings of the National Academy of Sciences 105.2 (2008): 686-691.
Wang, Y., et al., The hypoxia-inducible factor a pathway couples angiogenesis to osteogenesis during skeletal development. Journal of Clinical Investigation 117.6 (2007):1616.
Williams, E. A., et al., The early healing of tibial osteotomies stabilized by one-plane or two-plane external fixation. J Bone Joint Surg Am 69.3 (1987): 355-365.
Kalamazoo College 2015-2016 Academic Catalog. Obtained from http://www.kzoo.edu/catalog/KalamazooCollegeAcademicCatalog2015-16.pdf on Feb. 9, 2021, originally published Sep. 3, 2015, 150 printed pages.
Samir S. Deshpande. "Implantable Deferoxamine-Hyaluronic Acid Nanoparticle Promotes Angiogenesis and Accelerates Bone Regeneration." Kalamazoo College, Thesis. Fall 2015, p. i-vi and pp. 1-26 (32 total sheets).
Kalamazoo College Academic Registrar. Accessed at http://web.archive.org/web/201509051133/https://reason.kzoo.edu/registrar/dates/ accessed Oct. 30, 2020, published Sep. 5, 2015, 2 printed pages.
Kalamazoo College. https://cache.kzoo.edu/handle/10920/30358 accessed Oct. 13, 2020, originally published May 14, 2016, 4 printed pages.
Y Ikeda, et al. "Deferoxamine promotes angiogenesis via the activation of vascular endothelial cell function." Atherosclerosis 215 (2011) 339-347.
Y. Parajo, et al. "Hyaluronic acid/Chitosan nanoparticles as delivery vehicles for VEGF and PDGF-BB" Drug Delivery, 2010, 17(8): 596-604.

\* cited by examiner

DEVICES, COMPOSITIONS AND RELATED METHODS FOR ACCELERATING AND ENHANCING BONE REPAIR

CROSS-REFERENCE TO RELATED APPLICATIONS

This application is a continuation of U.S. patent application Ser. No. 16/063,061, filed Jun. 15, 2018, allowed as U.S. Pat. No. 11,045,556, which is a Section 371 U.S. national stage entry of International Patent Application No. PCT/US2016/067320, International Filing Date Dec. 16, 2016, which claims priority to and the benefit of U.S. Provisional Application No. 62/268,926, filed Dec. 17, 2015, which are hereby incorporated by reference in their entireties.

STATEMENT REGARDING FEDERALLY SPONSORED RESEARCH OR DEVELOPMENT

This invention was made with government support under CA125187 and CA173292 awarded by the National Institutes of Health. The government has certain rights in the invention.

FIELD OF THE INVENTION

The present invention relates to novel therapeutic nanoparticles. In particular, the present invention is directed to nanoparticles associated (e.g., complexed, conjugated, encapsulated, absorbed, adsorbed, admixed) with angiogenesis-activating-agents, methods of synthesizing the same, devices or compositions comprising such nanoparticles, as well as systems and methods utilizing the nanoparticles (e.g., in therapeutic settings for enhancing and/or activating angiogenesis at targeted tissue region).

BACKGROUND OF THE INVENTION

Head and neck cancers (HNC) impose a significant biomedical burden by accounting for over 8000 deaths and 50,000 new cases each year. HNC patients often require multimodality treatment with surgery, radiation (XRT), and chemotherapy. Although XRT has increased survival it also results in damage to adjacent normal tissues leading to significant morbidity. The corrosive impact of these XRT-induced side effects can be unrelenting and their complex management is rarely remedial. Severely problematic wound healing issues impact the reconstructive efforts to replace the bone and soft tissue removed by tumor extirpation and the options to treat XRT-induced pathologic fractures and osteoradionecrosis. Standard of care currently dictates complex mandibular reconstruction utilizing free tissue transfer from other parts of the body requiring extended hospitalizations. Attendant complications often lead to delays in initiation of therapy jeopardizing prognosis as well as quality of life. Advances in biotechnology have afforded a unique opportunity to innovate new remedies for XRT-induced side effects by bringing novel and more effective therapeutic strategies into the actual operating theater. Distraction Osteogenesis (DO), the creation of new bone by the gradual separation of two osteogenic fronts, generates an anatomical and functional replacement of deficient tissue from local substrate and could have immense potential for reconstruction after oncologic resection. XRT drastically impairs fracture healing, however, precluding the utilization of DO as a durable reconstructive method for HNC. Innovative solutions to remedy the deleterious effects of XRT on bone formation would allow successful regeneration of the mandible and restore the capacity for normal bone healing. New treatment strategies for bone repair are needed in order to develop applications that can be utilized synchronously with operative reconstruction, to fundamentally transform current surgical paradigms. Specific metrics of diminished bone quality at the healing interface of irradiated mandibles have been demonstrated. In addition, technologies have been developed that function to assuage the adverse impact of XRT induced injury. Such technologies demonstrated remediation of the XRT-induced degradation of bone healing. The consequential finding of such findings was the ability to generate new bone formation and a bony union in scenarios where this was not previously possible. These innovative solutions enable the translation of such findings from the bench to the operative suite to improve the treatment for severely compromised patient populations.

SUMMARY

Experiments conducted during the course of developing embodiments for the present technology resulted in the development of a hyaluronic acid nanoparticle conjugated with an agent able to enhance and/or activate angiogenesis (e.g., DFO). For example, such experiments resulted in the development of a hyaluronic acid—DFO nanoparticle (HA-DFO). It was shown that HA-DFO is a conjugate of biocompatible-bioabsorbable hyaluronic acid that conjugates and detoxifies the iron-chelator DFO. It was shown that when DFO is covalently conjugated to the carboxylate of HA, the immobilized DFO-HA becomes a high-capacity iron sponge that prevents iron infiltration into the fracture site. It was found that 215 kDa and 750 kDa conjugates of Hyaluronic Acid (HA) bound to DFO retained 95% and 85%, respectively, of the unmodified DFO's binding capacity for iron, and the conjugate was highly degradable by bovine hyaluronidase, indicating that the formation of the conjugate is primed for customized release. The nano-DFO formulation (750 kDa, 13% DFO by weight) was further shown to have no toxicity in human umbilical vein endothelial cells (HUVECs) at 10 µM, whereas non-bound, free DFO reduced cell viability by nearly 60%. In vivo efficacy of nano-DFO was further demonstrated. Given that the peak for angiogenesis kinetics is around 10-14 days after bone injury, it was shown that delivering DFO in a sustained release manner over 2-4 weeks provides an improved drug delivery solution to maximize therapeutic effect. In addition, it was shown that the anti-inflammatory properties of HA include improved healing by minimizing tissue destruction secondary to inflammation (see, e.g, Baldini, Alberto, et al., Annali di stomatologia 1.1 (2010): 2). This nanoparticle therapy is designed to work alone or in concert with the baseline therapeutic standard of internal fixation of bony fractures.

Accordingly, the present invention is directed to nanoparticles associated (e.g., complexed, conjugated, encapsulated, absorbed, adsorbed, admixed) with angiogenesis-activating-agents, methods of synthesizing the same, devices or compositions comprising such nanoparticles, as well as systems and methods utilizing the nanoparticles (e.g., in therapeutic settings for enhancing and/or activating angiogenesis at targeted tissue region).

In certain embodiments, the present invention provides devices or compositions comprising a nanoparticle associated with an angiogenesis-activating-agent.

Such devices or compositions are not limited to a particular type or kind of nanoparticle. In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, any nanostructures, microstructures, or their derivatives formed using layer-by-layer processes, self-assembly processes, or polyelectrolytes, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, carboxymethylcellulose and related mixtures, polysaccharides, polyamino acids, poly-acrylates, poly-alcohols (e.g. poly vinyl alcohol), polyesters (e.g. poly caprolactones), pluronics, pullulans, and a modified micelle.

In some embodiments, the nanoparticle is a hyaluronic acid (HA) nanoparticle.

Such devices or compositions are not limited to a particular type or kind of angiogenesis-activating-agent. In some embodiments, the angiogenesis-activating-agent is able to increase and/or activate angiogenesis upon administration to a subject. In some embodiments, the angiogenesis-activating-agent is able to increase HIF-1α activity upon administration to a subject. In some embodiments, the angiogenesis-activating-agent is able to inhibit prolyl hydroxylation of HIF-1α upon administration to a subject. In some embodiments, the angiogenesis-activating-agent is able to remove iron upon administration to a subject. In some embodiments, the angiogenesis-activating-agent is able to increase VEGF transcription upon administration to a subject. In some embodiments, the angiogenesis-activating-agent is able to increase bone morphogenic protein (BMP) activity upon administration to a subject. In some embodiments, the angiogenesis-activating-agent is able to upregulate osteogenesis activity upon administration to a subject.

In some embodiments, the angiogenesis-activating-agent is deferoxamine (DFO) (N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide).

In some embodiments, the present invention provides a device or composition described by

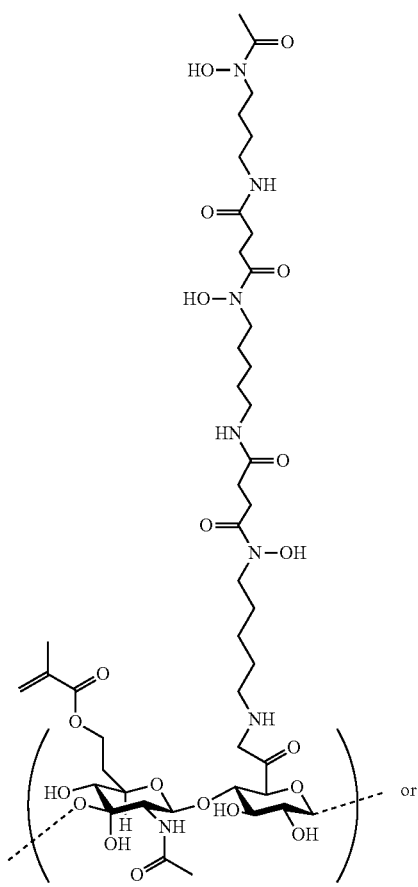

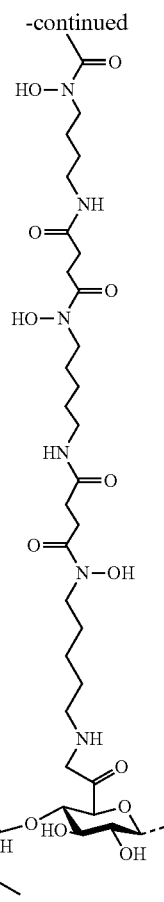

Such devices or compositions are not limited to a particular manner of associating an angiogenesis-activating agent with a nanoparticle.

In some embodiments, the angiogenesis-activating agent is complexed with the nanoparticle. As used herein, the term "complexed" relates to the non-covalent interaction of the angiogenesis-activating agent with the nanoparticle.

In some embodiments, the angiogenesis-activating agent is conjugated with the nanoparticle. As used herein, the term "conjugated" indicates a covalent bond association between the angiogenesis-activating agent and the nanoparticle.

In some embodiments, the angiogenesis-activating agent is encapsulated within the nanoparticle. As used herein, the term "encapsulated" refers to a location of the angiogenesis-activating agent that is enclosed or completely contained within the inside of a nanoparticle.

In some embodiments, the angiogenesis-activating agent is adsorbed with the nanoparticle. As used herein, the term "absorbed" refers to an angiogenesis-activating agent that is taken into and stably retained in the interior, that is, internal to the outer surface, of a nanoparticle.

In some embodiments, the angiogenesis-activating agent is adsorbed with the nanoparticle. As used herein, the term "adsorbed" refers to the attachment of an angiogenesis-activating agent to the external surface of a nanoparticle. Such adsorption preferably occurs by electrostatic attraction. Electrostatic attraction is the attraction or bonding generated between two or more oppositely charged or ionic chemical groups. Generally, the adsorption is typically reversible.

In some embodiments, the angiogenesis-activating agent is admixed with the nanoparticle. As used herein, the term "admixed" refers to an angiogenesis-activating agent that is dissolved, dispersed, or suspended in a nanoparticle. In some cases, the angiogenesis-activating agent may be uniformly admixed in the nanoparticle.

In some embodiments, the device or composition comprising a nanoparticle associated with (e.g., complexed, conjugated, encapsulated, absorbed, adsorbed, admixed) an angiogenesis-activating-agent is lyophilized.

In certain embodiments, such devices and compositions are used for therapeutic purposes involving the treatment, prevention, and/or amelioration of a bone fracture.

For example, in some embodiments, methods for treating a subject's bone fracture, comprising administering to a subject having a bone fracture a therapeutically effective amount of such devices or compositions are provided.

In some embodiments, methods for accelerating and/or activating angiogenesis at a subject's bone fracture, comprising administering to the subject having a bone fracture a therapeutically effective amount of such devices or compositions are provided.

In some embodiments, methods for inducing osteogenesis at a subject's bone fracture, comprising administering to the subject having a bone fracture a therapeutically effective amount of such devices or compositions are provided.

In some embodiments, methods for increasing HIF-1α activity at a subject's bone fracture, comprising administering to the subject having a bone fracture a therapeutically effective amount of such devices or compositions are provided.

In some embodiments, methods for removing iron at a subject's bone fracture, comprising administering to the subject having a bone fracture a therapeutically effective amount of such devices or compositions are provided.

In some embodiments, methods for increasing VEGF transcription at a subject's bone fracture, comprising administering to the subject a having bone fracture a therapeutically effective amount of such devices or compositions are provided.

In some embodiments, methods for increasing BMP activity at a subject's bone fracture, comprising administering to the subject having a bone fracture a therapeutically effective amount of such devices or compositions are provided.

In some embodiments, methods for inducing osteogenesis at a subject's bone fracture, comprising administering to the subject having a bone fracture a therapeutically effective amount of such devices or compositions are provided.

Such methods are not limited to a particular type of subject. In some embodiments, the subject is a mammalian subject. In some embodiments, the subject is a non-human mammalian subject. In some embodiments, the subject is a human being. In some embodiments, the subject is suffering from one or more of the following disorders: osteoradionecrosis, avascular necrosis, diabetes, non-union, delayed bone healing, failed bone grafting, malunion, pathologic fracture, failed surgical bony fusions or fusions or fractures at high risk of failure, and a ballistic injury.

Such methods are not limited to a particular dosage or amount of a therapeutically effective amount of the device or composition. In some embodiments, the amount of device or composition is approximately 215 kDa of HA conjugated with DFO. In some embodiments, the amount of device or composition is approximately 750 kDa of HA conjugated with DFO.

In certain embodiments, the present invention provides kits comprising such a device or composition and instructions for administering the device or composition to a subject.

DETAILED DESCRIPTION OF THE INVENTION

Figure 1:
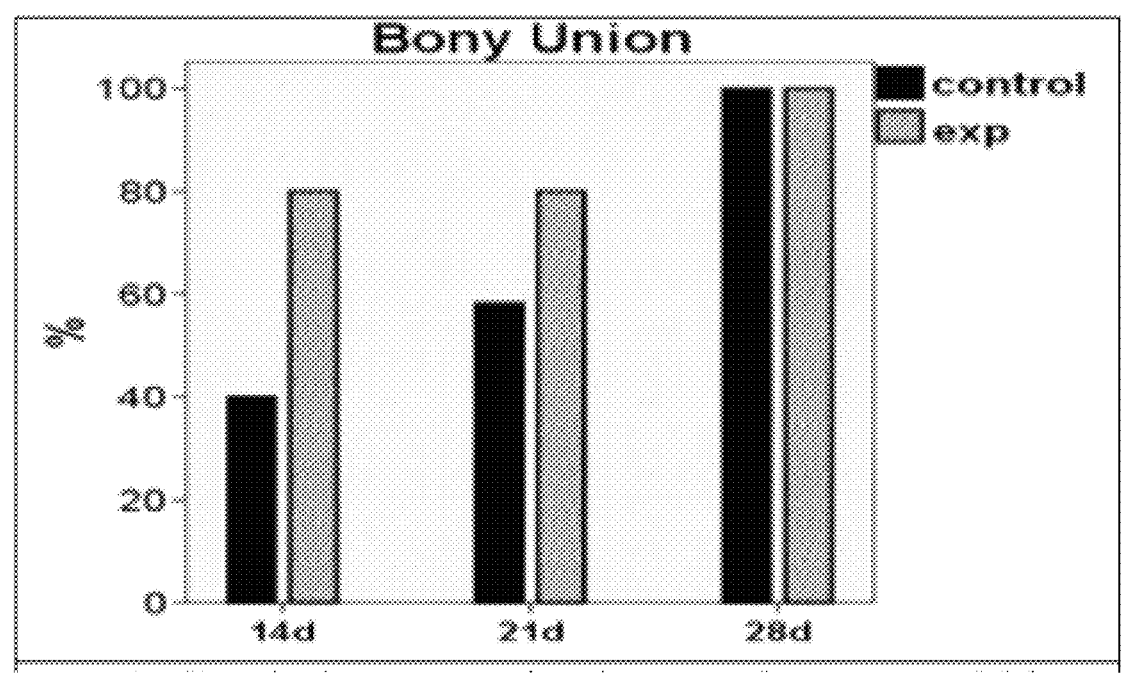
FIG. 1: Graph demonstrating bony union rates within groups. Note the doubling of bony unions in the experimental group at 14 d when compared to the non-treated controls. At 21 d, control union rate increased by 20%; however, experimental union rate remained increased by comparison. By 28 days, both groups exhibited 100% bony union rate.

The elaborate involvement of the vascular system during bone healing makes it a clear target for therapeutic optimization. It is generally accepted that bone repair involves a series of events that are innately dependent on an initial escalation of angiogenesis that functions to supply the rigorous metabolic demands required to heal osseous tissues (see, e.g., Hunter J: Treatise on the Blood, Inflammation, and Gunshot Wounds. Philadelphia, Thomas Bradford 1794; Trueta J, J Bone Joint Surg 45B:402-418, 1963; Rhinelander F W, Clin Orthop 105:34-49, 1974; Cavadias A X, Trueta J, Surg Gynecol Obstet 120:731-747, 1965; Kelly P J, et al., Clin Orthop 254275-288, 1990; Laumen E L, Kelly P J, J Bone Joint Surg 51A:298-308, 1969; Rhinelander F W, J Bone JointSurg50A:784-800, 1968, Brighton C T, Hunt R M, J BoneJointSurg73A:832-847, 1991). Early on, the increased metabolic demand is related to the formation of a thrombus and the breakdown and removal of necrotic bone. Later, this metabolic toll is related to the importation of cellular and extracellular elements to the site of bone healing that culminate in the formation of a soft callus, its transition to a hard callus and eventual remodeling. Overall, the timely and accurate reconstitution of bone and the overall success of bone healing is dependent largely on blood supply and stability. In fact, these two are intimately related, as excessive motion across a fracture gap can tear delicate new vessels before their protection by calcified tissue (see, e.g., Glowacki, Julie, Clinical orthopaedics and related research 355 (1998) S82-S89).

Transient and localized increases in callus blood circulation secondary to bone injury make the site of bone healing a favorable environment for therapeutic exploitation. Investigators have demonstrated an increase in blood flow that peaks at 7-14 days after fracture (see, e.g., Glowacki, Julie, Clinical orthopaedics and related research 355 (1998): S82-S89; Aronson, James, Clinical orthopaedics and related research 301 (1994): 124-131; Williams, E. A., et al., J Bone Joint Surg Am 69.3 (1987): 355-365). Conceptually, therapeutic manipulation of the callus site around this time-period may allow for early triggering and sustenance of angiogenic responses that lead to accelerated fracture healing. DFO, an iron chelator, has a demonstrated capacity to increase angiogenesis via the hypoxia inducible factor (HIF 1-α) pathway (see, e.g., Wang, Ying, et al., Journal of Clinical Investigation 117.6 (2007):1616). DFO triggers a transcriptional cascade of events by favoring the accumulation of HIF 1-α. Iron is a co-factor required for the prolyl hydroxylation of HIF 1-α—a reaction that leads to its ultimate degradation (see, e.g., Huang, L., et al., Proceedings of the National Academy of Sciences 95.14 (1998): 7987-7992). DFO inhibits prolyl hydroxylation by removing iron from the environment. This localized iron chelation leads to the constitutive and sustained presence of HIF 1-α that subsequently causes the increased transcription of VEGF and other downstream angiogenic molecules, resulting in a variety of advantageous effects on the growth of new blood vessels (see, e.g., Harten, et al., Antioxidants & redox signaling 12.4 (2010): 459-480; Liu, Xiaodong, et al., Cell biochemistry and biophysics 69.1 (2014): 141-149) The activation of VEGF is a critical step at the interface of angiogenesis and osteogenesis, as it not only triggers new blood vessel formation, but also stimulates the release of bone morphogenic proteins (BMPs) from endothelial cells, thereby indirectly upregulating osteogenesis (see, e.g., Beamer, Brandon, et al., HSS journal 6.1 (2010): 85-94; Towler, Dwight A., Current osteoporosis reports 6.2 (2008): 67-71). Utilizing this approach to augment angiogenesis, the ability to accelerate normal fracture healing and distraction osteogenesis (bone regeneration) in long bone animal models has been demonstrated (see, e.g., Shen, Xing, et al., Journal of orthopaedic research: official publication of the Orthopaedic Research Society 27.10 (2009): 1298; Wan, Chao, et al., Proceedings of the National Academy of Sciences 105.2 (2008): 686-691; Street, John, et al., Proceedings of the National Academy of Sciences 99.15 (2002): 9656-9661). This strategy has also been used to both accelerate craniomaxillofacial bone regeneration in distraction osteogenesis (DO) and to enable pathologic fracture healing after blood vessel injury utilizing multiple injections of DFO in the rat mandible (see, e.g., Farberg, Aaron S., et al., Plastic and reconstructive surgery 133.3 (2014): 666-671; Farberg, Aaron S., et al., Bone 50.5 (2012): 1184-1187; Felice, Peter A., et al., Plastic and reconstructive surgery 132.4 (2013): 542e; Donneys, Alexis, et al., Bone 55.2 (2013): 384-390; Donneys, Alexis, et al., Head & neck (2015); Donneys, Alexis, et al., Plastic and Reconstructive Surgery 131.5S (2013): 141; Donneys, Alexis, et al., Bone 52.1 (2013): 318-325; Donneys, Alexis, et al. Plastic and reconstructive surgery 131.5 (2013): 711e).

Although these results are promising, there are inherent limitations to the acceptance of this therapy for clinical use. Presently, the delivery of DFO to a fracture site via multiple localized injections is a convoluted process that may preclude its use in human patients (see, e.g., Kuchler, Ulrike, et al., Clinical oral implants research 26.5 (2015): 485-491; Segar, Claire E., et al., Current pharmaceutical design 19.19 (2013): 3403-3419). Currently, localized injections are administered directly into a fracture site through the overlying skin. Typically, multiple injections are required over a prolonged period of time to achieve the expected result. Inherent drawbacks to the use of multiple injections include: (1) associated pain and morbidity, (2) rapid systemic clearance with very little drug retained at the fracture site, and (3) potential introduction of infection into the wound bed. Furthermore, with the recent understanding of the timing and distribution of vascular growth at fracture sites, drug delivery could be improved to coincide with maximal angiogenic stimulation.

The present invention provides an improvement over the existing technology. Indeed, the present invention provides nanoparticles associated with (e.g., complexed, conjugated, encapsulated, absorbed, adsorbed, admixed) agents able to enhance and/or activate angiogenesis. Experiments conducted during the course of developing embodiments for the present technology allowed development of a hyaluronic acid nanoparticle conjugated with an agent able to enhance and/or activate angiogenesis (e.g., DFO).

For example, such experiments resulted in the development of a hyaluronic acid—DFO nanoparticle (HA-DFO). It was shown that HA-DFO is a conjugate of biocompatible-bioabsorbable hyaluronic acid that conjugates and detoxifies the iron-chelator DFO. It was shown that when DFO is covalently conjugated to the carboxylate of HA, the immobilized DFO-HA becomes a high-capacity iron sponge that prevents iron infiltration into the fracture site. It was found that 215 kDa and 750 kDa conjugates of Hyaluronic Acid (HA) bound to DFO retained 95% and 85%, respectively, of the unmodified DFO's binding capacity for iron, and the conjugate was highly degradable by bovine hyaluronidase, indicating that the formation of the conjugate is primed for customized release.

The nano-DFO formulation (750 kDa, 13% DFO by weight) was further shown to have no toxicity in human umbilical vein endothelial cells (HUVECs) at 10 μM, whereas non-bound, free DFO reduced cell viability by nearly 60%. In vivo efficacy of nano-DFO was further demonstrated. Given that the peak for angiogenesis kinetics is around 10-14 days after bone injury, it was shown that delivering DFO in a sustained release manner over 2-4 weeks provides an improved drug delivery solution to maximize therapeutic effect. In addition, it was shown that the anti-inflammatory properties of HA are improved healing by minimizing tissue destruction secondary to inflammation (see, e.g, Baldini, Alberto, et al., Annali di stomatologia 1.1 (2010): 2). This nanoparticle therapy is designed to work alone or in concert with the baseline therapeutic standard of internal fixation of bony fractures.

Moreover, such findings revealed a synergistic effect for a combination of HA-DFO. Indeed, it was found that mixing the DFO with HA resulted in a more pronounced effect than either drug alone. In addition, it was also noted that the DFO actually made the HA degrade slower which improved the duration of drug delivery. In comparison with the known properties for HA and DFO alone, such findings are quite novel, non-obvious and unexpected.

Accordingly, the present invention is directed to nanoparticles associated (e.g., complexed, conjugated, encapsulated, absorbed, adsorbed, admixed) with angiogenesis-activating-agents, methods of synthesizing the same, devices or compositions comprising such nanoparticles, as well as systems and methods utilizing the nanoparticles (e.g., in therapeutic settings for enhancing and/or activating angiogenesis at targeted tissue region).

Such therapeutic nanoparticles are not limited to a particular manner of associating an angiogenesis-activating agent with a nanoparticle.

In some embodiments, the angiogenesis-activating agent is complexed with the nanoparticle. As used herein, the term "complexed" relates to the non-covalent interaction of the angiogenesis-activating agent with the nanoparticle.

In some embodiments, the angiogenesis-activating agent is conjugated with the nanoparticle. As used herein, the term "conjugated" indicates a covalent bond association between the angiogenesis-activating agent and the nanoparticle.

In some embodiments, the angiogenesis-activating agent is encapsulated within the nanoparticle. As used herein, the term "encapsulated" refers to a location of the angiogenesis-activating agent that is enclosed or completely contained within the inside of a nanoparticle.

In some embodiments, the angiogenesis-activating agent is adsorbed with the nanoparticle. As used herein, the term "absorbed" refers to an angiogenesis-activating agent that is taken into and stably retained in the interior, that is, internal to the outer surface, of a nanoparticle.

In some embodiments, the angiogenesis-activating agent is adsorbed with the nanoparticle. As used herein, the term "adsorbed" refers to the attachment of an angiogenesis-activating agent to the external surface of a nanoparticle. Such adsorption preferably occurs by electrostatic attraction. Electrostatic attraction is the attraction or bonding generated between two or more oppositely charged or ionic chemical groups. Generally, the adsorption is typically reversible.

In some embodiments, the angiogenesis-activating agent is admixed with the nanoparticle. As used herein, the term "admixed" refers to an angiogenesis-activating agent that is dissolved, dispersed, or suspended in a nanoparticle. In some cases, the angiogenesis-activating agent may be uniformly admixed in the nanoparticle.

In some embodiments, the device or composition comprising a nanoparticle associated with (e.g., complexed, conjugated, encapsulated, absorbed, adsorbed, admixed) an angiogenesis-activating-agent is lyophilized.

Such therapeutic nanoparticles are not limited to a particular type or kind of nanoparticle.

In some embodiments, the nanoparticle is selected from the group consisting of sHDL nanoparticle, fullerenes, endohedral metallofullerenes buckyballs, trimetallic nitride templated endohedral metallofullerenes, single-walled and mutli-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, any nanostructures, microstructures, or their derivatives formed using layer-by-layer processes, self-assembly processes, or polyelectrolytes, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, carboxymethylcellulose and related mixtures, polysaccharides, polyamino acids, polyacrylates, poly-alcohols (e.g. poly vinyl alcohol), polyesters (e.g. poly caprolactones), pluronics, pullulans, and a modified micelle.

In some embodiments, the nanoparticle and angiogenesis-activating-agent is suspended, admixed or complexed with an additional polymer, matrix, or excipient or mixture of the above, to extend its retention at the injection site. For example, in some embodiments, the nanoparticle is associated with non-covalent cross linkers. Such non-covalent cross linkers include, but are not limited to, polycations to crosslink polyanionic materials (e.g., hyaluronan, CMC), protamine, spermine, spermidine, chitosan, poly-lysine, and divalent and trivalent ions, such as MgCl2, MgAcetate2, Calcium Chloride, Calcium carbonate. In some embodiments, the nanoparticle is associated with solubility reducers such as oleic acid, and other lipophilic and fatty acids and phospholipids.

In some embodiments, the nanoparticle is a modified micelle. In these embodiments, the modified micelle comprises polyol polymers modified to contain a hydrophobic polymer block. The term "hydrophobic polymer block" as used in the present disclosure indicates a segment of the polymer that on its own would be hydrophobic. The term "micelle" as used herein refers to an aggregate of molecules dispersed in a liquid. A typical micelle in aqueous solution forms an aggregate with the hydrophilic "head" regions in contact with surrounding solvent, sequestering the hydrophobic single tail regions in the micelle centre. In some embodiments the head region may be, for example, a surface region of the polyol polymer while the tail region may be, for example, the hydrophobic polymer block region of the polyol polymer.

In some embodiments, the nanoparticle is a hyaluronic acid (HA) nanoparticle.

Hyaluronic acid, also referred to as "HA," is a naturally occurring, water soluble polysaccharide that is a major component of the extra-cellular matrix and is widely distributed in animal tissues. Naturally occurring HA generally has a molecular weight range of about between $6 \times 10^4$ to about $8 \times 10^6$ Daltons. It has excellent biocompatibility and does not give a foreign body or allergic reaction when implanted into a subject.

Methods of preparing commercially available HA are well known. Also known are various methods of coupling HA and cross-linking HA to reduce the water solubility and diffusibility of HA, and to increase the viscosity of HA (see, e.g., U.S. Pat. Nos. 5,356,883 and 6,013,679). Further, many forms of HA have been employed, e.g., as surgical aids to prevent post operative adhesions of tissues, as adjuncts to synovial fluid in joints, as fluid replacement and/or surgical aids in ophthalmic surgery, as a scaffold for tissue engineering in vitro or guided tissue regeneration or augmentation in vivo, and the like.

Hyaluronic acid [hyaloid (vitreous)+uronic acid] (HA) was isolated for the first time in 1934 from the vitreous humor of bovine eyes (see, e.g., Meyer, K.; Palmer, J. W., J. Biol. Chem. 1934, 107, 629-634). It is a naturally occurring linear polysaccharide with repeating units of D-glucuronic acid and N-acetyl-D-glucosamine disaccharide:

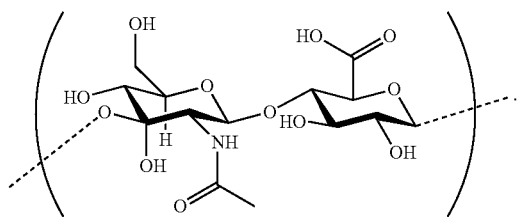

The pKa of HA carboxyl groups is 3-4; at pH=7, these groups being ionized, the hyaluronan molecule is a polyanion associated with cations (the counterions). HA is a highly hydrophilic polymer that can absorb a large amount of water and expand up to 1000 times its solid volume, forming a loose hydrated network (see, e.g., Laurent, T. C., et al., FASEB J. 1992, 6, 2397-2404). The molar mass of HA can be as high as 10 MDa, and such a molar mass accounts for the important physiological roles of HA in living organism, including maintenance of the viscoelasticity of liquid connective tissues (such as synovial fluid in the joints or eye vitreous humor), control of tissue hydration, water transport, proteoglycan organization in the extracellular matrix (ECM), tissue repair and various receptor-mediated functions in cell detachment, tumor development and inflammation (see, e.g., Cowman, M. K., et al., Carbohydr. Res. 2005, 340, 791-809).

In the field of drug delivery, HA has become a carrier of great interest owing to its advantages, like: (i) biodegradability; (ii) biocompatibility; (iii) ease of chemical modification; (iv) high potential drug loading; and (v) its intrinsic targeting properties, due to the selective interactions with receptors.

The chemical modification of HA can be performed on its carboxylate for purposes of conjugation with a drug (see, e.g., Schanté, C. E., et al., Carbohydr. Polym. 2011, 85, 469-489). Conjugation of drugs to HA involves formation of a pro-drug by covalently binding a drug to the HA backbone through a bond that ideally should be stable during the blood circulation and promptly cleaved at a specific target site.

In certain embodiments, the present invention provides a hyaluronic acid—"angiogenesis-activating-agent" conjugate in which the angiogenesis-activating-agent is conjugated with a carboxyl group of hyaluronic acid. For example, in certain embodiments, the present invention provides the following hyaluronic acid—angiogenesis-activating-agent conjugate formula:

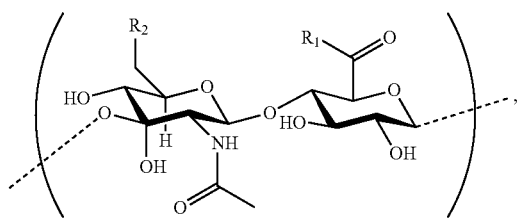

wherein R1 is an angiogenesis-activating-agent, and R2 is methylacrylate or hydroxyl. In some embodiments, a linker bridges the conjugation between the angiogenesis-activating-agent and the carboxylate of the hyaluronic acid.

Such embodiments are not limited to a particular angiogenesis-activating-agent. In some embodiments, the angiogenesis-activating-agent is any agent that is able to increase and/or activate angiogenesis at a desired tissue region. In some embodiments, the angiogenesis-activating-agent is any agent that is able to increase HIF-1α activity at a desired tissue region. In some embodiments, the angiogenesis-activating-agent is any agent that is able to inhibit prolyl hydroxylation of HIF-1α at a desired tissue region. In some embodiments, the angiogenesis-activating-agent is any agent that is able to remove iron from a desired tissue region. In some embodiments, the angiogenesis-activating-agent is any agent that is able to increase VEGF transcription at a desired tissue region. In some embodiments, the angiogenesis-activating-agent is any agent that is able to increase bone morphogenic protein (BMP) activity at a desired tissue region. In some embodiments, the angiogenesis-activating-agent is any agent that is able to upregulate osteogenesis activity at a desired tissue region.

In some embodiments, the angiogenesis-activating-agent is deforoxamine (DFO) (N'-{5-[Acetyl(hydroxy)amino]pentyl}-N-[5-({4-[(5-aminopentyl)(hydroxy)amino]-4-oxobutanoyl}amino)pentyl]-N-hydroxysuccinamide). For example, in some embodiments, the following HA-DFO nanoparticle is provided:

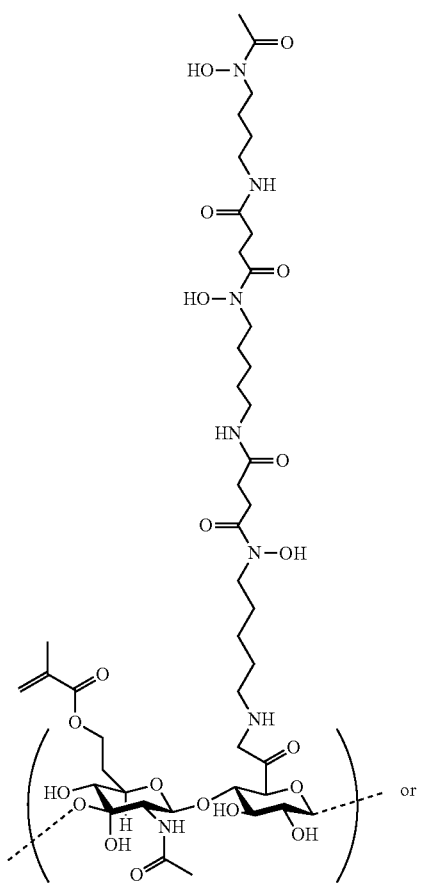

or

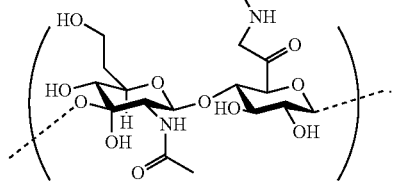

As described, in some embodiments, a linker bridges the conjugation between the angiogenesis-activating-agent (e.g., DFO) and the carboxylate of the hyaluronic acid. Such embodiments are not limited to a particular linker or use of a linker. In some embodiments, the linker assists in targeting the nanoparticle to a region requiring angiogenesis (e.g., a bone fracture).

In some embodiments, the nanoparticle is further associated with (e.g., complexed, conjugated, encapsulated, absorbed, adsorbed, admixed) a chemical moiety permitting sustained-release of the angiogenesis-activating-agent (e.g., over a period of minutes, hours, days, weeks, months, etc.).

In some embodiments, the nanoparticle is further associated with (e.g., complexed, conjugated, encapsulated, absorbed, adsorbed, admixed) a targeting agent. The present invention is not limited to any particular targeting agent. In some embodiments, targeting agents are associated with (e.g., complexed, conjugated, encapsulated, absorbed, adsorbed, admixed) the nanoparticle for delivery to desired body regions (e.g., to a bone fracture site requiring angiogenesis activation). The targeting agents are not limited to targeting specific body regions. In some embodiments of the present invention, the targeting agent includes, but is not limited to an antibody, receptor ligand, hormone, vitamin, and an antigen.

In some embodiments, the nanoparticle is further associated with (e.g., complexed, conjugated, encapsulated, absorbed, adsorbed, admixed) an imaging agent. A multiplicity of imaging agents find use in the present invention. In some embodiments, the nanoparticle comprises at least one imaging agent that can be readily imaged. The present invention is not limited by the nature of the imaging component used. In some embodiments of the present invention, imaging modules comprise surface modifications of quantum dots (see, e.g., Chan and Nie, Science 281:2016 (1998)) such as zinc sulfide-capped cadmium selenide coupled to biomolecules (see, e.g., Sooklal, Adv. Mater., 10:1083 (1998)). In some embodiments, once a component(s) of a nanoparticle (e.g., HA-DFO) has attached to (or been internalized into) a region requiring activation of angiogenesis (e.g., a bone fracture), one or more modules can serve to image its location. In some embodiments, chelated paramagnetic ions, such as Gd(III)-diethylenetriaminepentaacetic acid (Gd(III)-DTPA), are conjugated to the nanoparticles. Other paramagnetic ions that may be useful in this context include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof.

In some embodiments, imaging agents associated with (e.g., complexed, conjugated, encapsulated, absorbed, adsorbed, admixed) the nanoparticle are designed to emit light or other detectable signals upon exposure to light. Although the labeled functional groups may be physically smaller than the optical resolution limit of the microscopy technique, they become self-luminous objects when excited and are readily observable and measurable using optical techniques. In some embodiments, sensing fluorescent biosensors in a microscope involves the use of tunable excitation and emission filters and multiwavelength sources (see, e.g., Farkas et al., SPEI 2678:200 (1997)). In embodiments where the imaging agents are present in deeper tissue, longer wavelengths in the Near-infrared (NMR) are used (see e.g., Lester et al., Cell Mol. Biol. 44:29 (1998)). Biosensors that find use with the present invention include, but are not limited to, fluorescent dyes and molecular beacons.

In some embodiments, in vivo imaging is accomplished using functional imaging techniques. Functional imaging is a complementary and potentially more powerful technique as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce when excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue. In some embodiments, fluorescent groups such as fluorescein are employed in the imaging agent. Fluorescein is easily attached to the nanoparticle surface via the isothiocyanate derivatives, available from MOLECULAR PROBES, Inc.

The nanoparticles of the present invention find a variety of therapeutic uses. For example, in some embodiments, the nanoparticles associated with (e.g., complexed, conjugated, encapsulated, absorbed, adsorbed, admixed) an angiogenesis-activating-agents finds use in accelerating and/or enhancing bone repair (e.g., bone repair of a fractured bone) by activating angiogenesis at the tissue region requiring bone repair. In some embodiments, the nanoparticles associated with (e.g., complexed, conjugated, encapsulated, absorbed, adsorbed, admixed) an angiogenesis-activating-agents find use in accelerating and/or enhancing bone regeneration (e.g., bone regeneration of a fractured bone) by activating angiogenesis at the tissue region requiring bone regeneration.

Such methods are not limited to a particular manner of accelerating and/or enhancing bone repair or regeneration. In some embodiments, the nanoparticles associated with (e.g., complexed, conjugated, encapsulated, absorbed, adsorbed, admixed) an angiogenesis-activating-agents are able to increase and/or activate angiogenesis at the tissue region. In some embodiments, such nanoparticles associated with angiogenesis-activating-agents are able to increase HIF-1α activity at the tissue region. In some embodiments, such nanoparticles associated with angiogenesis-activating-agents are able to inhibit prolyl hydroxylation of HIF-1α at the desired tissue region. In some embodiments, such nanoparticles associated with angiogenesis-activating-agents are able to remove iron from the desired tissue region. In some embodiments, such nanoparticles associated with angiogenesis-activating-agents are able to increase VEGF transcription at the desired tissue region. In some embodiments, such nanoparticles associated with angiogenesis-activating-agents are able to increase bone morphogenic protein (BMP) activity at the desired tissue region. In some embodiments such nanoparticles associated with angiogenesis-activating-agents are able to upregulate osteogenesis activity at the desired tissue region.

In some embodiments, methods are provided for treating a subject's bone fracture, comprising administering to the subject a therapeutically effective amount of a device or composition comprising a nanoparticle associated with (e.g., complexed, conjugated, encapsulated, absorbed, adsorbed, admixed) an angiogenesis-activating-agent (e.g., a hyaluronic acid based nanoparticle conjugated with an angiogenesis-activating-agent). In some embodiments, the angiogenesis-activating-agent is deferoxamine (DFO).

In some embodiments, methods are provided for accelerating and/or activating angiogenesis at a subject's bone fracture, comprising administering to the subject a therapeutically effective amount of device or composition comprising a nanoparticle associated with (e.g., complexed, conjugated, encapsulated, absorbed, adsorbed, admixed) an angiogenesis-activating-agent (e.g., a hyaluronic acid based nanoparticle conjugated with an angiogenesis-activating-agent). In some embodiments, the angiogenesis-activating-agent is deferoxamine (DFO).

In some embodiments, methods are provided for inducing osteogenesis within a subject, comprising administering to the subject a therapeutically effective amount of device or composition comprising a therapeutically effective amount of a composition comprising a nanoparticle associated with (e.g., complexed, conjugated, encapsulated, absorbed, adsorbed, admixed) an angiogenesis-activating-agent (e.g., a hyaluronic acid based nanoparticle conjugated with an angiogenesis-activating-agent). In some embodiments, the angiogenesis-activating-agent is deferoxamine (DFO).

In some embodiments, methods are provided for increasing HIF-1α activity at a desired tissue region within a subject, comprising administering to the subject a therapeutically effective amount of device or composition comprising a nanoparticle associated with (e.g., complexed, conjugated, encapsulated, absorbed, adsorbed, admixed) an angiogenesis-activating-agent (e.g., a hyaluronic acid based nanoparticle conjugated with an angiogenesis-activating-agent). In some embodiments, the angiogenesis-activating-agent is deferoxamine (DFO).

In some embodiments, methods are provided for removing iron at a desired tissue region within a subject, comprising administering to the subject a therapeutically effective amount of device or composition comprising a nanoparticle associated with (e.g., complexed, conjugated, encapsulated, absorbed, adsorbed, admixed) an angiogenesis-activating-agent (e.g., a hyaluronic acid based nanoparticle conjugated with an angiogenesis-activating-agent). In some embodiments, the angiogenesis-activating-agent is deferoxamine (DFO).

In some embodiments, methods are provided for increasing VEGF transcription at a desired tissue region within a subject, comprising administering to the subject a therapeutically effective amount of device or composition comprising a nanoparticle associated with (e.g., complexed, conjugated, encapsulated, absorbed, adsorbed, admixed) an angiogenesis-activating-agent (e.g., a hyaluronic acid based nanoparticle conjugated with an angiogenesis-activating-agent). In some embodiments, the angiogenesis-activating-agent is deferoxamine (DFO).

In some embodiments, methods are provided for increasing BMP activity at a desired tissue region within a subject, comprising administering to the subject a therapeutically effective amount of device or composition comprising a nanoparticle associated with (e.g., complexed, conjugated, encapsulated, absorbed, adsorbed, admixed) an angiogenesis-activating-agent (e.g., a hyaluronic acid based nanoparticle conjugated with an angiogenesis-activating-agent). In some embodiments, the angiogenesis-activating-agent is deferoxamine (DFO).

Such methods are not limited to a particular subject. In some embodiments, the subject is a mammal (e.g., cow, pig, horse, dog, cat, human being, etc.). In some embodiments, the subject is a mammal having a fracture bone. In some embodiments, the subject is a mammal experiencing a diminished ability to heal a fractured bone (e.g., the mammal is further suffering from osteoradionecrosis, avascular necrosis, diabetes, advanced age, non-union, malunion, pathologic fracture, failed surgical bony fusions or fusions or fractures at high risk of failure, ballistic injuries, etc.).

Such methods are not limited to a particular "therapeutically effective amount" for the device or composition comprising a nanoparticle associated with (e.g., complexed, conjugated, encapsulated, absorbed, adsorbed, admixed) an angiogenesis-activating-agent (e.g., a hyaluronic acid based nanoparticle conjugated with an angiogenesis-activating-agent). Indeed, such an amount can readily be determined by a professional. In some embodiments, the device or composition comprises 215 kDa of HA conjugated with DFO. In some embodiments, the device or composition comprises 750 kDa of HA conjugated with DFO.

In certain embodiments, such methods further involve co-administration with one or more additional therapeutic agents. Such embodiments are not limited to a particular additional therapeutic agent. In some embodiments, the additional therapeutic agent is an additional angiogenesis-activating-agent. In some embodiments, the additional therapeutic agent is a pain management therapeutic agent. In some embodiments, the additional therapeutic agent is an infection inhibiting agent. In some embodiments, the additional therapeutic agent is an agent for treating, preventing and/or ameliorating osteoradionecrosis. In some embodiments, the additional therapeutic agent is an agent for treating, preventing and/or ameliorating avascular necrosis.

In some embodiments, the additional therapeutic agent is an agent for treating, preventing and/or ameliorating diabetes. In some embodiments, the additional therapeutic agent is an agent for treating, preventing and/or ameliorating non-union related bone disorders and/or conditions. In some embodiments, the additional therapeutic agent is an agent for treating, preventing and/or ameliorating delayed bone healing. In some embodiments, the additional therapeutic agent is an agent for treating, preventing and/or ameliorating failed bone grafting. In some embodiments, the additional therapeutic agent is an agent for treating, preventing and/or ameliorating malunion related bone disorders and/or conditions. In some embodiments, the additional therapeutic agent is an agent for treating, preventing and/or ameliorating pathologic fracture. In some embodiments, the additional therapeutic agent is an agent for treating, preventing and/or ameliorating failed surgical bony fusions. In some embodiments, the additional therapeutic agent is an agent for treating, preventing and/or ameliorating fusions or fractures at high risk of failure.

In certain embodiments, the present invention also provides kits comprising a device or composition comprising a nanoparticle associated with (e.g., complexed, conjugated, encapsulated, absorbed, adsorbed, admixed) an angiogenesis-activating-agent. In some embodiments, the nanoparticle is a hyaluronic acid based nanoparticle. In some embodiments, the angiogenesis-activating-agent is deferoxamine (DFO). In some embodiments, the kit further comprises one or more additional therapeutic agents.

EXPERIMENTAL

The following examples are provided in order to demonstrate and further illustrate certain preferred embodiments and aspects of the present invention and are not to be construed as limiting the scope thereof.

Example I

This example demonstrates that DFO accelerates bone regeneration in maxillofacial distraction osteogenesis.

Figure 2:
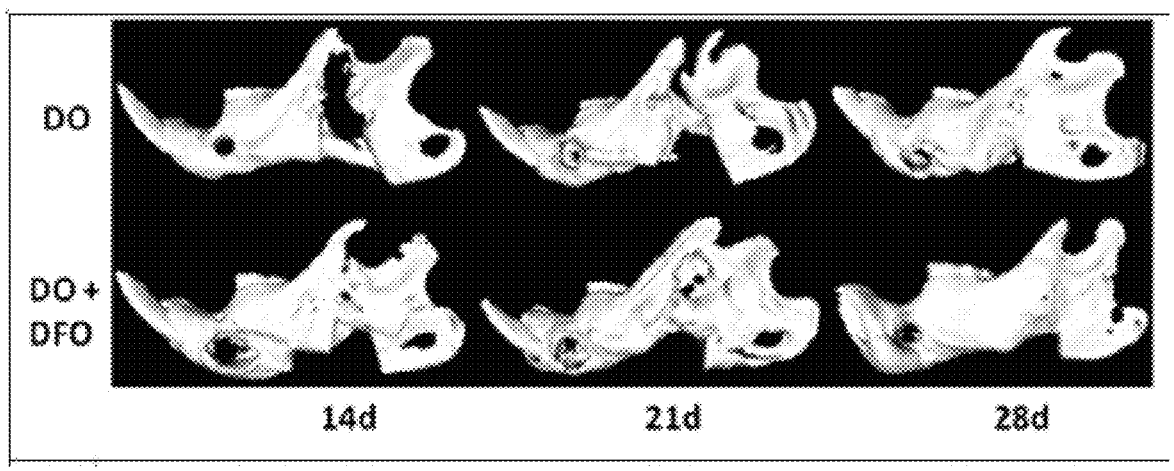
FIG. 2: Select μCT images demonstrating the DO group (top row) and the DO+DFO group (bottom row) at each time point. At the earlier 14 d and 21 d time-points, note the visible augmentation in regenerate radiodensity in the treatment group indicative of accelerated consolidation and healing with therapy.

The effectiveness of DFO in enhancing regenerate vascularity at a full consolidation period (28 days) in a murine mandibular DO model was established. To investigate whether this augmentation in vascularity would function to accelerate consolidation without compromising regenerate quality or strength, consolidation periods prior to μCT imaging and biomechanical testing (BMT) were progressively shortened. Three time points (14 d, 21 d and 28 d) were selected and six groups of Sprague-Dawley rats (n=60) were equally divided into control (C) and experimental (E) groups for each time period. Each group underwent external fixator placement, mandibular osteotomy, and a 5.1 mm distraction. During distraction, the experimental groups were treated with DFO injections into the regenerate gap. After consolidation, mandibles were imaged and tension tested to failure. ANOVA was conducted between groups, and $p<0.05$ was considered statistically significant. At 14 days of consolidation the E group demonstrated significant increases in Bone Volume Fraction (BVF), Bone Mineral Density (BMD) and Ultimate Load (UL) in comparison to non-treated controls (FIG. 1). The benefit of treatment was further substantiated by a striking 100% increase in the number of clinically appreciated bony unions at this early time-period (C:4/10 vs. E:8/10, FIG. 2) (see, e.g., Donneys, Alexis, et al., Bone 55.2 (2013): 384-390). Furthermore, metrics of BVF, BMD, Yield and UL at 14 days with treatment demonstrated comparable metrics to those of the fully consolidated 28 d control group. Based on these findings, it was contended that augmentation of vascular density through localized DFO injection delivers an efficient means for accelerating bone regeneration without significantly impacting bone quality or strength.

Example II

This example demonstrates that DFO augments fracture healing in the irradiated mandible.

The effects of radiation on bone formation and healing are mediated through the mechanisms of vascular damage, direct cellular depletion and diminished function of osteocytes. Over time, this accumulated damage predisposes patients to the debilitating problem of late pathologic fractures and non-unions. Here, the use of DFO was employed to bolster the vascular response during bone healing in this setting. It was posited that the untoward effects of radiotherapy on vascular density and osteocyte count and ultimately the mineralization and biomechanical strength of our bone would be improved with the addition of DFO. 12 rats received fractionated radiotherapy to left hemi-mandibles. After recovery, fracture repair ensued with external fixator placement and mandibular osteotomy. DFO was injected into the callus site every other day from post-operative days 4-12. A 40-day healing period was allowed prior to vessel perfusion, PCT, BMT, and histologic processing. Mandibles were dissected and gross union was assessed. Union was defined as bony bridging and the absence of motion across the fracture site. Outcome data was analyzed with ANOVA, and $p \leq 0.05$ was statistically significant. The DFO group was compared with two other groups: fracture-Fx and radiated fracture-XFx (n=12, 12).

Figure 3:
FIG. 3: 3D reconstructed μCT angiograms of rat mandibles showing the fracture sites from Fx (top), XFx (middle), and DFO-treated radiated fracture mandibles (bottom). Vessels are highlighted in the region of interest and the surrounding mandible is superimposed for visual localization and clarity.

Results: Vascularity: The DFO treated group demonstrated a significant restoration to control level Vessel Volume when compared to XFx (p=0.029). Vessel Number, Thickness and Separation also showed significant restorative effects (FIG. 3).

Histomorphometry: Histology revealed a significant restoration to control level osteocyte count (p=0.000); and a corresponding decrease in empty lacunae (p=0.000) when comparing DFO-treated to XFx.

BMT and Mineralization: The DFO-treated animals demonstrated a significant increase in all of the metrics when compared to the XFx group. Additionally, there was no difference seen between the Fx and the DFO-treated groups, suggesting a restoration to control levels.

Bony Union: While Fx mandibles demonstrated 100% bony union, XFx mandibles only demonstrated 25% union. The DFO group demonstrated 67% bony union. Ultimately, a complete restoration of vascular density and osteocyte count with the addition of DFO was observed. The most consequential finding was a 42% increase in bony unions in a model where healing was not routinely observed (see, e.g., Donneys, Alexis, et al., Bone 52.1 (2013): 318-325; Donneys, Alexis, et al., Plastic and reconstructive surgery 131.5 (2013): 711e).

Example III

This example demonstrates a real-time investigation of the angiogenic effect of deferoxamine on endothelial cells exposed to radiotherapy.

Figure 4:
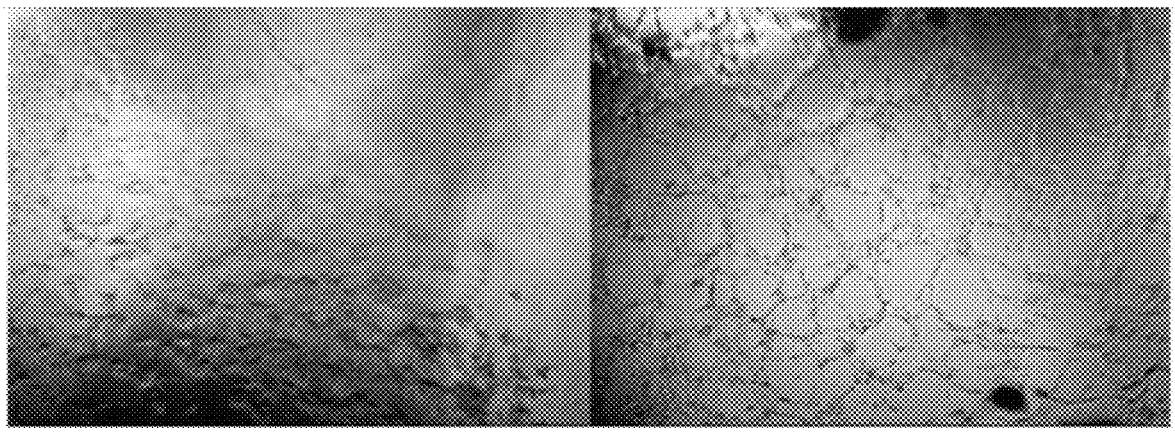
FIG. 4: Endothelial cells in matrigel angiogenic media after two hours of incubation. (Left): Cells exposed to radiation demonstrate poor organization and aggregation. (Right): Cells treated with DFO demonstrate visible organization and formation of a robust vascular network despite exposure to radiation.

The effect of DFO on endothelial cells exposed to radiation in vitro was investigated. It was posited that radiation would significantly diminish the ability of endothelial cells to form tubules; and subsequently, that the addition of DFO would effect a restoration of tubule formation. Four groups of human umbilical vein endothelial (HUVEC) cells (control, radiated, radiated+low dose DFO, or radiated+high dose DFO) were incubated in Matrigel and video recorded in real-time over 12 hours. DFO groups received either 25 or 50 μM doses at the time of incubation. Tubule formation was photographed at 100× magnification every four hours. Tubule numbers between groups were compared using ANOVA with $p \leq 0.05$ considered statistically significant. A severe diminution in endothelial tubule formation after radiotherapy was observed. Specifically, tubule formation was diminished 30%, 34%, and 27% respectively, compared to control values (p=0.01, at 4, 8, and 12 hours). The effects of radiation were strikingly remediated by treatment with high-dose DFO. High dose DFO cells demonstrated organized tubule formation that was significantly increased in comparison to radiated cells (p=0.02 at 4, 8, and 12 hours), and reached or exceeded normal levels at each respective time point. These findings were clearly observed with real-time recording. High-dose DFO cultures appeared to organize within 2 hours of incubation and achieved a robust vascular network that was visibly superior to all other experimental groups in an accelerated fashion (FIG. 4). This evidence supports the contention that DFO strongly remediates the effects of radiation on endothelial tubule formation (see, e.g., Donneys, Alexis, et al., Plastic and Reconstructive Surgery 131.5S (2013): 141).

Example IV

Figure 5:
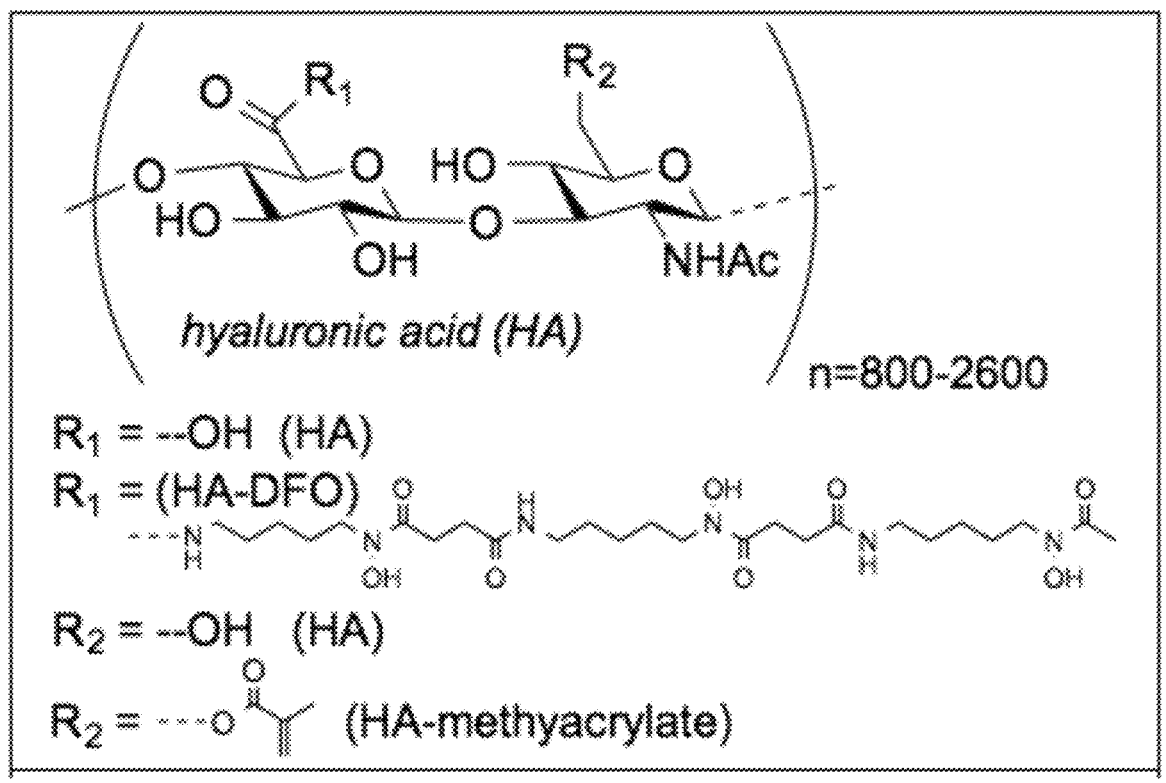
FIG. 5: HA-DFO is produced by conjugating HA (0.2-1 MDa) and DFO (10-15% w/w) using EDC. The resulting conjugate has an in vitro half-life of over 2 weeks and retains>85% of free DFO's capacity to chelate free Fe (III). HA-DFO will be crosslinked to slow enzymatic degradation and sustain free tissue retention, using either epoxide or methyacrylate chemistries.

Nano-DFO is a conjugate of biocompatible-bioabsorbable hyaluronic acid (HA) that conjugates and detoxifies iron-chelator DFO. When DFO is covalently conjugated to the carboxylate of HA, the immobilized DFO-HA becomes a high-capacity iron sponge that prevents infiltration into the fracture site (FIG. 5). As the terminal amine of DFO is uninvolved in formation of the Fe(III)-chelates, it was found that 215-kDa and 750-kDa conjugates of HA to DFO (10-13% wt/wt DFO) retained 95 and 85%, respectively, of the unmodified DFO's binding capacity for Fe(III). Unmodified and crosslinked HAs are currently FDA-approved as dermal fillers and intraarticular injections for osteoarthritis. Unmodified HA is cleared in <1 wk from the tissue spaces by lymphatics and endogenous hyaluronidases, followed by further hepatic and renal clearance. Highly crosslinked and chemically modified HAs of several MDa's are resistant to rapid degradation and clearance. Crosslinked HAs of >1 MDa can have resident times from several months (e.g. Restylane®) to a year (e.g. Juvederm Ultra Plus®), depending on the extent of crosslinking.

HA-DFO (750 kDa HA, 13% wt DFO) in HUVEC cells, HA-DFO was shown to have no toxicity at 10 μM (DFO basis) whereas free DFO reduced cell viability by ca. 60%. The conjugate was highly degradable by bovine testis hyaluronidase.

Figures 6A, 6B:
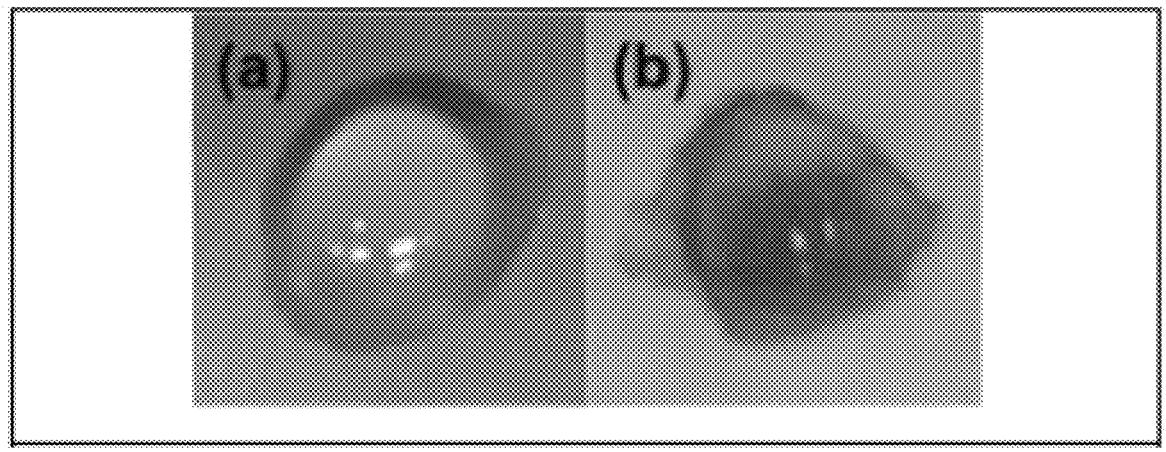
FIG. 6A-B: HA-DFO-methylacrylate can be UV-photocrosslinked to form a semi-firm gel with sustained tissue retention over weeks (A). On exposure to $FeCl_3$, the gel strongly chelates iron (B).

Uncrosslinked HA is rapidly cleared from the tissue space, with a halflife of about 24 hours. Dermal fillers based on HA are crosslinked to differing extents (5-20%) and with ether or ester crosslinkers to extend retention time from a few months (e.g. Captique®) to over 18 months (e.g. Juvederm Ultra 30HV®). HA-DFO was partially methacrylated using methacrylic anhydride (1-10% of free COOH groups) and photocrosslinked (365 nm) with Irgacure 2959 as an initiator using reported method, followed by extensive dialysis to remove unreacted crosslinker and initiator. Irgacure is not yet FDA approved for parenterals, but is approved for food applications. It was shown that the crosslinked product (structure confirmed by FTIR and NMR) strongly chelated Fe(III) and formed a semi-solid flowable gel (FIG. 6).

A highly crosslinked but injectable HA gel based on a diepoxide crosslinker was recently developed. The diepoxide forms ethers in the HA depending. The excess linker can be deactivated by brief hydrolysis treatment and removed to trace levels by dialysis of tangential flow filtration. This is a chemistry very similar to the FDA approved HA dermal filler Puragen®, which uses a 1,2,7,8-diepoxy crosslinker to form crosslinks and has a residence time of 6-8 months in subcutaneous tissues.

Example V

This example demonstrates that HA-DFO nanoparticles improve bone mineralization and biomechanical strength in irradiated fractures.

Pathologic fractures and associated non-unions arising in irradiated bone are complex management dilemmas for reconstructive surgeons. An implantable, sustained-release nanoparticle formulation of a known angiogenic small molecule Deferoxamine (DFO) (HA-DFO) was developed, which obviates the need for serial injections of standard DFO. The efficacy of nano-DFO as compared to standard DFO was investigated, in its ability to improve metrics of mineralization, mechanical strength and bony union.

Rats (n=44) were divided into 4 groups. Fracture, radiated fracture, radiated fracture with standard DFO and radiated fracture with nano-DFO. Radiated groups received radiotherapy 2 weeks prior to mandibular osteotomy. The nano-DFO group received implantation of the drug at the time of surgery. Following a 40-day healing period, mandibles were assessed for bony-union, imaged with µCT, and mechanically tested to failure. ANOVA was used for comparison and ($p<0.05$).

Figure 7:
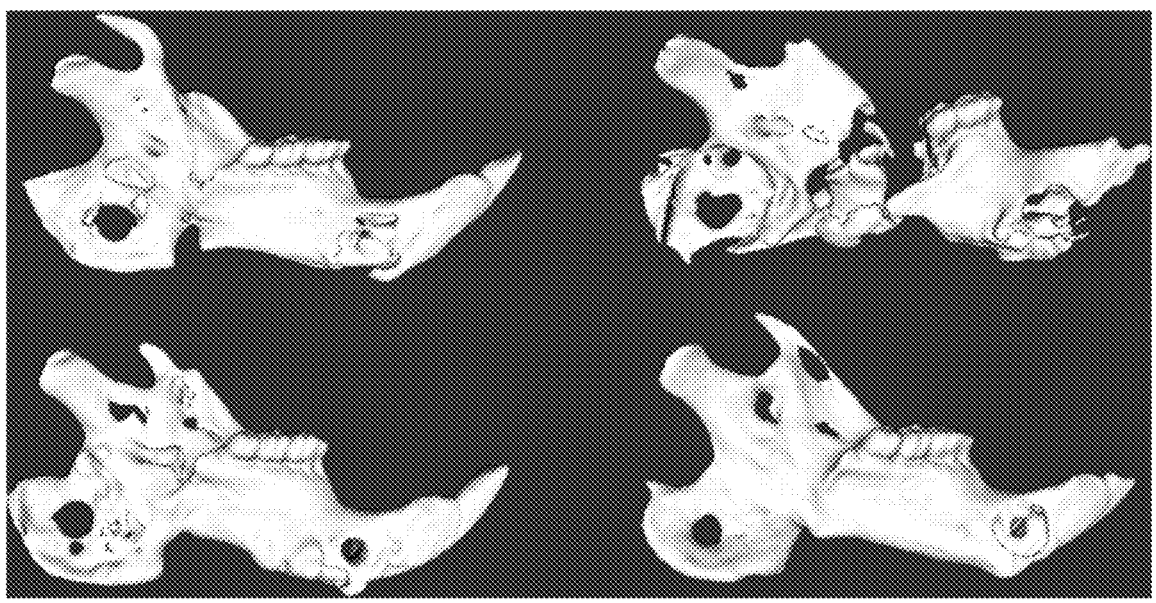
FIG. 7: Select μCT images as described in Example V.
Figure 8:
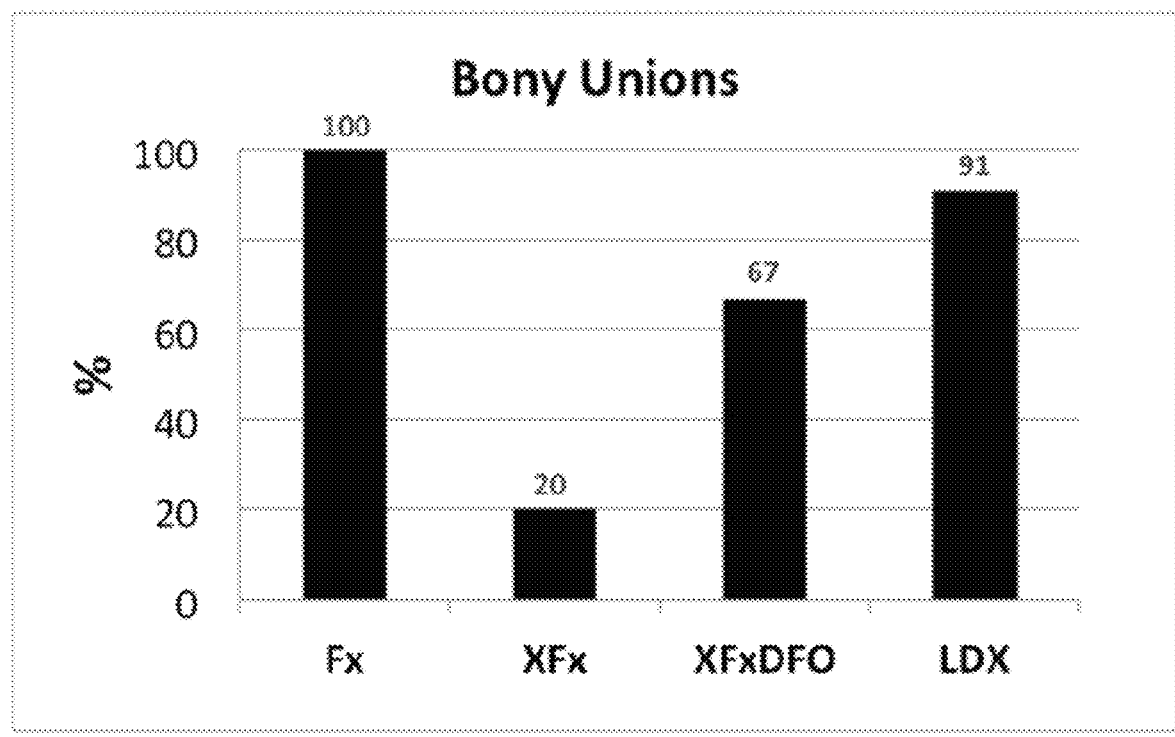
FIG. 8: Bony Union table as described in Example V.

Decreases in all metrics for the radiation group were remediated with the addition of both DFO and nano-DFO therapies. For metrics of BMD, TMD, BVF, Stiffness and Failure Load, there was no difference between the two treatments (See FIG. 7). However, there was a clinically relevant increase in Bony Unions with nano-DFO therapy that was 24% higher than standard DFO (67% vs. 91%; FIG. 8).

The data demonstrate in vivo efficacy for the mineralization and biomechanical properties of implanted nano-DFO when compared to normal DFO. The continued investigation of this promising treatment in its translation for the management of pathologic fractures and associated non-unions after radiotherapy was demonstrated.

Example VI

This example describes the investigation of the remediation of angiogenesis following radiation exposure utilizing a novel angiogenic nanotechnology (HA-DFO).

Although radiotherapy is often necessary in oncologic management, it inhibits angiogenesis, leading to devastating consequences in adjacent healthy tissues. Deferoxamine (DFO) has been demonstrated to bolster angiogenesis following radiotherapy, but its delivery via multiple localized injections is suboptimal for clinical use. To remedy this, an implantable nanoparticle formulation of DFO was developed (HA-DFO). It was posited that the administration of nano-DFO (HA-DFO) will effect an in vitro restoration of angiogenesis comparable to normal DFO.

Three groups of irradiated (5Gy) endothelial cells (n=4/group) were divided according to the type of therapy they received (50 µM DFO, 50 µM nano-DFO and 100 µM nano-DFO). All cultures were video recorded simultaneously at 150× magnification over four hours. Hourly tubule counts between groups were compared using ANOVA with $p<0.05$ considered statistically significant.

Figure 9:
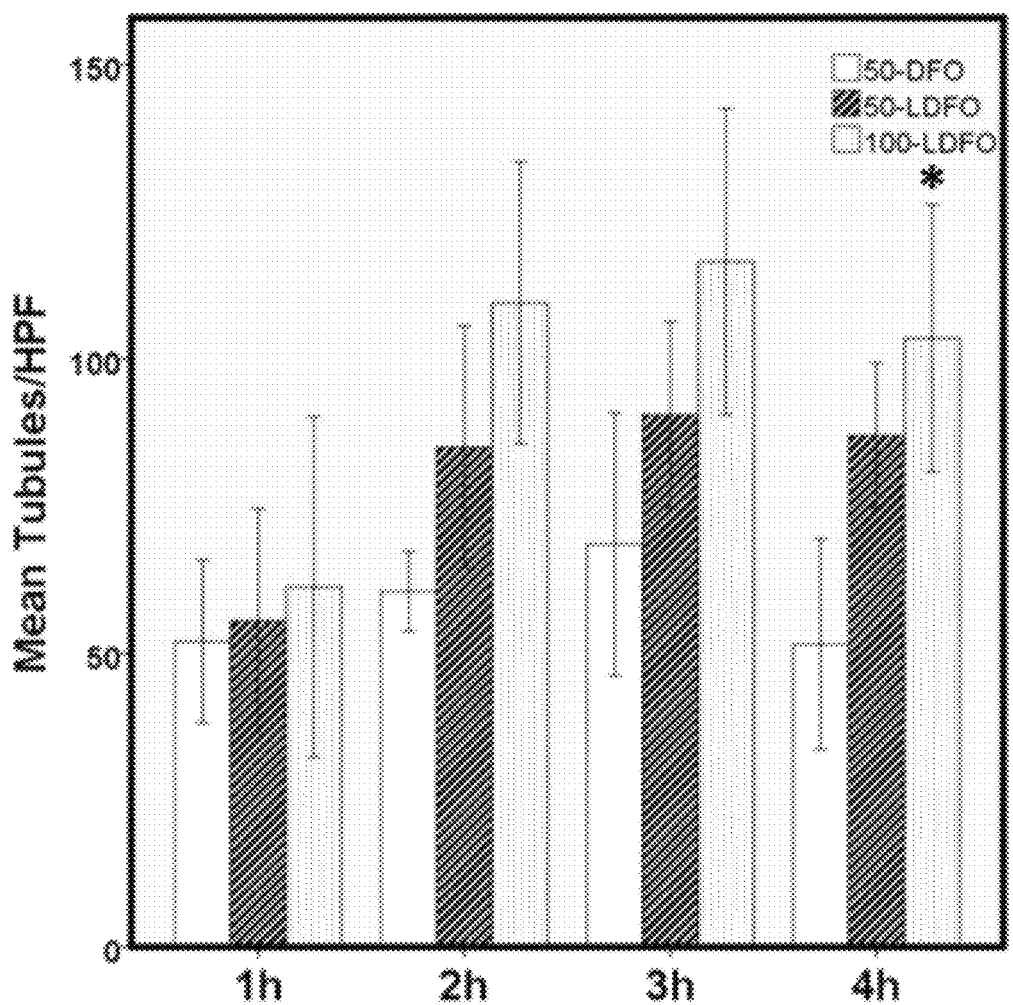
FIG. 9: Mean tubles/HPF as a function of time as described in Example VI.
Figure 10:
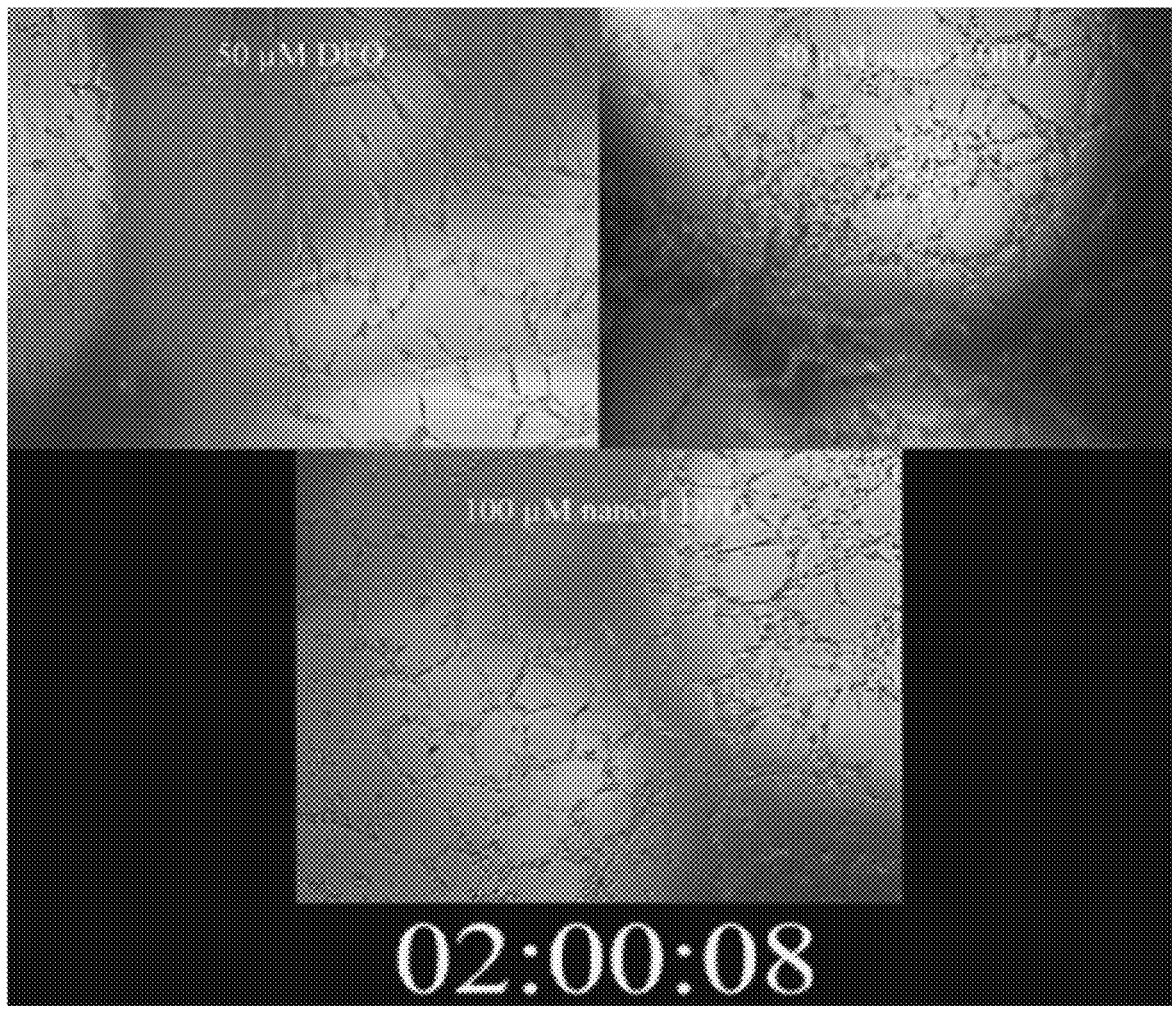
FIG. 10: An image showing vascular networks as described in Example VI.

No statistical differences between normal DFO and nano-DFO for any doses through 3 hours was observed. There were, however, trending increases between 50 µM DFO and 100 µM nano-DFO at 2 and 3 hours (p=0.055 and 0.066). Furthermore, a statistical increase between 50 µM DFO and 100 µM nano-DFO at 4 hours was observed (p=0.033, FIG. 9). Within two hours of incubation, 100 µM nano-DFO cultures appeared to achieve more robust vascular networks than the other experimental groups (FIG. 10).

The data establishes in vitro efficacy for the angiogenic potential of a novel nano-DFO formulation when compared to normal DFO.

Example VII

This example describes the mitigation of radiation induced injury in non-vascularized bone graft reconstruction of the murine mandible using a deferoxamine nanoparticle.

Mandible reconstruction following cancer resection and adjuvant radiation therapy necessitates increasingly complex methods of reconstruction. Vascularized free tissue transfer of osteocutaneous flaps exemplify the pinnacle of our current surgical techniques and remains the gold standard for oncologic reconstruction of the mandible following radiation therapy. However, these microvascular operations are complex, resource intensive, and introduce significant donor site morbidity. Non-vascularized bone grafts represent a formidable alternative means of reconstruction given their simplicity and ample donor substrate but are fraught with complications following radiation therapy.

These experiments investigated the efficacy of an implantable deferoxamine nanoparticle (nDFO) to remediate radiation induced injury and improve metrics of biomechanical strength and bony union during segmental bone grafting of the mandible.

Male Isogenic Lewis rats (n=42) were divided into 4 groups: bone graft donor (n=6), control bone graft (n=12), radiated bone graft (n=12), radiated bone graft+nDFO (n=12). Radiated groups received radiotherapy 2 weeks prior to surgery. Segmental osteotomy of the retromolar region of the mandible was performed and reconstructed with a 5 mm iliac crest bone graft harvested from the donor group. The nDFO group received implantation of the drug into the bone graft site at the time of surgery. Following a 40-day healing period, mandibles were dissected and assessed for bony union and biomechanically tested (BMT) to failure on a servo-hydraulic load cell. Chi Square was used for bony union rates ($\chi^2<0.05$) and ANOVA for BMT analysis ($p<0.05$).

Bony union rates were significantly diminished in the radiated bone graft group (42%) vs control (80%, p=0.04). This decrease in bony union was significantly remediated in the radiated bone graft+nDFO group (92%, p=0.01). There was no difference in bony union rates between control bone graft and radiated bone graft+nDFO (p=0.39). With biomechanical testing the radiated bone graft group demonstrated significant decreases in the metrics of stiffness (p=0.04), ultimate load (p=0.03), and failure load (p=0.04). Treatment with nDFO resulted in significant increases in the same metrics of stiffness (p=0.02), ultimate load (p=0.04), and failure load (p=0.05) compared to radiation alone.

These results demonstrate in-vivo efficacy of deferoxamine nanoparticle to significantly improve bony union rates and biomechanical properties of non-vascularized bone grafts in irradiated fields.

Example VIII

This example describes the preparation of $HA_{740k}$-DFO conjugate using DMTMM.

One hundred and fifty milligrams of sodium hyaluronate (HA, 740 KDa) was dissolved in 45-mL $H_2O$, and 4-(4,6-Dimethoxy-1,3,5-triazin-2-yl)-4-methylmorpholin-4-ium chloride (DMTMM, 309 mg, 1.12 mmol) was added. The resulted solution was gently stirred for 15 minutes at room temperature. An aqueous solution (5 mL) of deferoxamine mesylate salt (DFO, 245 mg, 0.37 mmol) was then added to the reaction mixture and pH of the resulted solution was adjusted to pH 5 using 1-N NaOH solution. The reaction mixture was then gently stirred for 48 hours at 37° C. The reaction mixture was purified by dialysis (10K MWCO) against 100-mM NaCl (3×) and Nanopure water (3×) for 48 hours. The resulted solution was then filtered (0.2 μm) and lyophilized to afford the HA-DFO as a white fluffy solid. Product was analyzed by 1HNMR in deuterium oxide. Degree of substitution was calculated using the peaks at 1.92 ppm (3H, HA) and 1.7-1.1 ppm (18H, DFO), and was found to be ~1.2% on a molar basis. When equal volume of HA-DFO (2 mg/mL) and $FeCl_3$ (3 mM) solutions were mixed, the solution was turned turbid immediately, and a dense light orange precipitate was formed after overnight incubation at room temperature.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A composition comprising a polymer and an agent,
   wherein the polymer is crosslinked with one or more chemical crosslinkers,
   wherein the agent is 1) an angiogenesis-activating agent, and 2) a chemical moiety capable of forming a chelate with iron,
   wherein the agent is immobilized with the polymer crosslinked with one or more crosslinkers,
   wherein the immobilization of the agent with the polymer limits release of the agent in an in vivo setting to a sustained release over a two to four week period.

2. The composition of claim 1, wherein the polymer is hyaluronic acid.

3. The composition of claim 1, wherein the chemical moiety comprises a plurality of chemical groups that comprise one or more amides and/or hydroxyamines.

4. The composition of claim 3, wherein the chemical moiety is a covalent conjugate of deferoxamine to the polymer.

5. The composition of claim 1, wherein the agent upon administration of the composition to a patient is capable of increasing bony union strength after radiation treatment.

6. The composition of claim 1, wherein the agent upon administration of the composition to a patient is capable of increasing tubule formation.

7. The composition of claim 1, wherein the one or more chemical crosslinkers is methylacrylate.

8. The composition of claim 1, wherein the one or more chemical crosslinkers is epoxide.

9. The composition of claim 1, wherein the weight percentage of the agent is 10-13% of that of the polymer.

10. A method for improving bony union strength, comprising administering to a subject the composition of claim 1.

11. A method of sequestering iron at the site of a bony fracture comprising administering to a subject the composition of claim 1.

* * * * *